United States Patent [19]

Patel et al.

[11] Patent Number: 5,759,527
[45] Date of Patent: Jun. 2, 1998

[54] HAIR CONDITIONING COMPOSITION

[75] Inventors: Amrit M. Patel, Dayton; Tracey A. Aldrich, Somerset, both of N.J.

[73] Assignee: Colgate-Palmolive Company, New York, N.Y.

[21] Appl. No.: 720,658

[22] Filed: Oct. 2, 1996

[51] Int. Cl.$^6$ ............................ A61K 7/06; A61K 7/075
[52] U.S. Cl. ........................ 424/70.11; 424/70.12; 424/70.13; 424/70.28
[58] Field of Search ............................ 424/70.11, 70.28, 424/70.13, 70.12

[56] References Cited

U.S. PATENT DOCUMENTS

| | | |
|---|---|---|
| 3,655,865 | 4/1972 | Murphy . |
| 4,035,478 | 7/1977 | Mullen . |
| 4,421,740 | 12/1983 | Burton . |
| 4,426,310 | 1/1984 | Verunica . |
| 4,610,874 | 9/1986 | Matravers . |
| 4,719,104 | 1/1988 | Patel . |
| 4,725,433 | 2/1988 | Matravers . |
| 4,726,945 | 2/1988 | Patel . |
| 4,728,375 | 3/1988 | Simpson . |
| 4,868,163 | 9/1989 | Takei . |
| 4,886,660 | 12/1989 | Patel . |
| 4,933,176 | 6/1990 | Van Reeth . |
| 4,954,335 | 9/1990 | Janchipraponvej . |
| 5,034,218 | 7/1991 | Duvel . |
| 5,077,042 | 12/1991 | Darkwa et al. . |
| 5,145,607 | 9/1992 | Rich . |
| 5,149,522 | 9/1992 | Schwarz et al. . |
| 5,227,163 | 7/1993 | Eini et al. . |
| 5,277,899 | 1/1994 | McCall . |
| 5,294,437 | 3/1994 | Shah . |
| 5,336,497 | 8/1994 | Guerrero . |
| 5,354,564 | 10/1994 | Borish et al. . |
| 5,374,420 | 12/1994 | Gerstein . |
| 5,384,334 | 1/1995 | Polovsky et al. . |
| 5,411,729 | 5/1995 | O'Lenick, Jr. . |
| 5,411,992 | 5/1995 | Eini et al. . |
| 5,439,674 | 8/1995 | Noda et al. . |
| 5,476,649 | 12/1995 | Naito et al. . |

FOREIGN PATENT DOCUMENTS

| | | |
|---|---|---|
| 306843 | 9/1988 | European Pat. Off. . |
| 339994 | 4/1989 | European Pat. Off. . |
| 429576 | 5/1990 | European Pat. Off. . |
| 0 407 042 B1 | 1/1991 | European Pat. Off. . |
| 556218 | 11/1991 | European Pat. Off. . |
| 592876 | 9/1993 | European Pat. Off. . |
| 0 635 260 | 1/1995 | European Pat. Off. . |
| 1 460 781 | 7/1970 | France . |
| 37 19293 A1 | 12/1987 | Germany . |
| 43 26 866 A 1 | 2/1995 | Germany . |
| 42-16957 | 9/1967 | Japan . |
| 50-52007 | 5/1975 | Japan . |
| 60-109514 | 6/1985 | Japan . |
| 61-130208 | 6/1986 | Japan . |
| 63-154613 | 3/1989 | Japan . |
| 64-56609 | 3/1989 | Japan . |
| 3-178917 | 8/1991 | Japan . |
| 5-201835 | 8/1993 | Japan . |
| 5-221839 | 8/1993 | Japan . |
| 07-69848 | 3/1995 | Japan . |
| 88/03016 | 5/1988 | WIPO . |
| 94/18934 | 9/1994 | WIPO . |

*Primary Examiner*—Sally Gardner-Lane
*Attorney, Agent, or Firm*—Rosemary M. Miano

[57] ABSTRACT

A single phase hair conditioning composition having improved hair conditioning properties is described which contains, by weight, about 0.8% to 1.4% of a water-soluble nonionic cellulose polymer thickener, about 0.5% to 2.0% of a dipolar solvent such as propylene glycol, about 0.2% to 3.0% of a mono-C12–C22 alkyl, monomethyl ethoxy substituted quaternary ammonium salt conditioning agent, about 0.2% to 2.5% of a C10–C18 alkyl ethoxy methyl carboxylic acid conditioning agent having 1 to 23 ethoxy groups in the molecule and an aqueous medium, said composition being free of water-insoluble alkanol conditioners and of conditioning amounts of silicone conditioners. The mixture of ethoxy substituted quaternary ammonium salt conditioner and ethoxy methyl carboxylic acid conditioner provides enhanced hair conditioning results. Preferred compositions include one of more of the following: a mono C8–C18 alkyl tri-C1–C3 alkyl quaternary ammonium salt conditioner, a water-soluble cationic polymer conditioner, an alkanol ethoxylate nonionic conditioner and a dimethicone copolyol. Also within the scope of the invention is the method of conditioning the hair which employs the foregoing single phase composition.

18 Claims, No Drawings

HAIR CONDITIONING COMPOSITION

TECHNICAL FIELD

The present invention relates to post shampoo hair conditioning compositions containing a water-soluble nonionic cellulose polymer thickening agent, a dipolar solubilizer and a hair conditioning mixture of a water-soluble mono-C12–C22 alkyl monomethyl ethoxy substituted quaternary ammonium salt conditioning agent having 10–20 ethenoxy groups in the molecule and a C10–C18 alkyl ethoxy methyl carboxylic acid having 1 to 23 ethenoxy groups in the molecule in an aqueous medium. Such compositions are single phase and are devoid of physical stability problems. One useful application of the inventive compositions is as a rinse-off hair conditioner.

BACKGROUND OF THE INVENTION

Currently, the popular creme rinse hair conditioners employ fatty alcohols such as cetyl and stearyl alcohol and a quaternary ammonium salt to provide conditioning properties. However, the fatty alcohols are not water-soluble and, therefore, must be emulsified with either nonionic or cationic surfactants in the product. Thus, the resultant products are opaque, sometimes lumpy and non-free flowing and often separate over a period of time because they are not thermodynamically stable.

Other rinse-off hair conditioner products utilize water-insoluble silicones as the conditioning agents. These products, too, must contain said silicones in emulsified form and, therefore, are opaque. Further, such products may separate with the passage of time due to a lack of physical stability.

Rinse-off hair conditioners which are single phase and devoid of problems of physical instability also have been employed. For example, U.S. Pat. No. 3,655,865 discloses a clear hair conditioning formulation containing oleyl dimethylbenzyl ammonium chloride conditioning agent, a water-soluble silicone copolyol and water. Chemical Abstracts 88-54977 and 89-11970e each discloses a single phase hair rinse product containing a water-soluble quaternary ammonium salt, an alkanol ethoxylate nonionic material, a lower alcohol or glycol and water. Each of U.S. Pat. No. 4,610,874 and U.S. Pat. No. 4,725,433 discloses in Example 1 a clear conditioner comprising hydroxyethyl cellulose, a mixture of cationic polymers—Polyquaternium 10 and Quaternium 23—, propylene glycol, polyvinylpyrrolidone and water. Similarly, U.S. Pat. No. 4,954,335 discloses in Example 6 a clear conditioner containing a di-higher alkyl quaternary ammonium salt conditioner, a soluble silicone, an amidoamine conditioner, a nonionic surfactant, hexylene glycol, hydroxyethyl cellulose and water. Finally, WO 94/18934 discloses in Example 1 a composition containing Polyquaternium 10, cetyl trimethyl ammonium chloride conditioner, dimethicone copolyol, nonionic surfactant and water. However, these single phase hair conditioning products provide only moderate conditioning effects and have not achieved widespread consumer acceptance.

In view of the foregoing discussion it is apparent that there is a need for a single phase hair conditioning product which provides high conditioning effects when employed as a rinse-off hair conditioning product.

SUMMARY OF THE INVENTION

It has been found that a hair conditioning composition comprising a mixture of a mono-C12–C22 alkyl quaternary ammonium salt having ethenoxy groups in the molecule, a C10–C14 alkyl ethoxy methyl carboxylic acid having 1–23 ethoxy groups in the molecule, a water-soluble nonionic cellulose thickener and a dipolar solvent dispersed in an aqueous medium which is primarily water provides a single phase composition which exhibits high hair conditioning effects when applied to the hair as a rinseoff conditioner.

Accordingly, a primary object of the present invention is to provide a single phase hair rinse conditioner which imparts high conditioning effects—softness and manageability, static control and ease of combing and styling—when applied to the hair after shampooing.

Another object of the present invention is to provide an economical hair rinse conditioner containing minimum concentrations of essential active ingredients which can be manufactured using low amounts of thermal energy.

To achieve the foregoing and other objects and in accordance with the present invention, the new and useful hair conditioning composition comprises, by weight, about 0.8% to 1.4% of a water-soluble nonionic cellulose polymer as a thickener; about 0.5% to about 2.0% of a dipolar solvent for the conditioning agents; 0.2% to about 3.0% of a water soluble, mono-C12–C22 alkyl, monomethyl ethenoxy substituted quaternary ammonium salt conditioning agent having 10–20 ethenoxy groups in the molecule; about 0.2% to 2.5% of a C10–C18 alkyl ethoxy methyl carboxylic acid having 1 to 23 ethoxy groups in the molecule; and the balance being an aqueous medium, said composition being free of water-insoluble C12–C22 alkanol conditioning agents and conditioning amounts of silicone conditioning agent. The final product is a clear liquid having a viscosity in the range of about 2,000 to 10,000 centipoises (cps) and a pH in the range of about 3.5 to about 4.3 at 24° C. The resultant composition exhibits better hair conditioning effects at use concentrations than identical compositions containing either of the essential hair conditioning agents as the sole hair conditioning agent.

In a preferred aspect, the present invention relates to a hair conditioning composition which includes, in addition, as an additional conditioning agent a hair conditioning agent selected from the group consisting of (a) about 0.05% to about 1.0% by weight of a water-soluble mono-C8–C22 alkyl tri-C1–C3 alkyl quaternary ammonium salt, (b) about 0.01% to about 1.5% of a water-soluble cationic polymer conditioning agent and (c) about 0.25% to about 5.0% of C10–C18 alkanol ethoxylate nonionic conditioning agent having an HLB in the range of 6.0 to 12.0 and (d) mixtures of the foregoing. The preferred compositions exhibit high hair conditioning effects when used as rinse-off hair conditioners.

In the most preferred aspect, from about 0.05% to about 5.0% by weight of a dimethicone copolyol is included as a shine agent.

The inventive compositions contain safe chemicals which are not irritating to the skin, are non-toxic and environmentally acceptable. Also, the compositions contain minimal concentrations of the essential components, yet provide good conditioning effects to the hair when employed as an after-shampoo conditioner. Further, said compositions can be manufactured with a minimal input of thermal energy.

DETAILED DESCRIPTION OF THE INVENTION

Hair Conditioning Agents

The suitable mono-C12–C22 alkyl, monomethyl ethoxylated quaternary ammonium salt conditioning agents employed in the inventive compositions have been used in the prior art as antistats in the treatment of textiles. They are water-soluble cationic surfactants. Generally, the suitable mono-higher alkyl ethoxylated quaternary ammonium salts have the following formula:

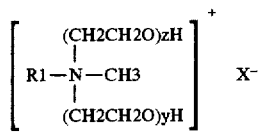

wherein R1 is a higher C12–C22 alkyl group, y and z are integers from 1 to 15 with the sum of y plus z being 10 to 20 and X is an anion selected from the group consisting of chloride, bromide, ethosulfate and methosulfate. The higher alkyl group may be a mixture of higher alkyl groups containing 12 to 22 carbon atoms. Representative examples of mono-higher alkyl ethoxylated quaternary ammonium salts include coco-alkyl (C8–C18) methyl ethoxylated (15) ammonium chloride, tallow-alkyl (C12–C18) methyl ethoxylated (15) ammonium chloride and polyoxyethylene (15) stearmonium chloride. Preferably, the higher alkyl group will contain 16 to 22 carbon atoms, with polyoxyethylene stearmonium chloride being most preferred. The latter compound is preferred and is described in the CTFA International Cosmetic Ingredient Dictionary as PEG-15 stearmonium chloride. It is purchased from Akzo as an 85% active liquid under the tradename Ethoquad® 18/25. The mono-C12–C22 alkyl, monomethyl ethoxylated quaternary ammonium salt is effective as a hair conditioner and is present in the inventive composition in an amount of about 0.2% to about 3.0%, preferably about 0.3% to about 2.2%, and most preferably about 0.5% to about 1.5%, by weight.

The other essential hair conditioning agent in the inventive compositions is a higher alkyl ether carboxylic acid. Generally, the alkyl ether carboxylic acid is a C10–C18 alkyl ethenoxy methyl carboxylic acid having 1 to 23 ethenoxy groups in the molecule. Suitable carboxylic acids include deceth-3 methyl carboxylic acid, laureth-3 methyl carboxylic acid, myreth-2 methyl carboxylic acid and, laureth-2 to 17 methyl carboxylic acid. These acids are described in the CTFA International Cosmetic Dictionary without reference to the methyl group, e.g., laureth-3 carboxylic acid. Such acids are available in liquid form. Preferably, said ethoxylated methyl carboxylic acid will contain 10 to 14 carbons in the alkyl group and 2 to 10 ethenoxy groups in the molecule. A preferred compound is laureth-3 methyl carboxylic acid which is purchased from Hoechst as a 93% active liquid. These materials have been used as a component in shampoos and in antiperspirants/deodorants, but are used herein as hair conditioning agents. The proportion of said carboxylic acid in the inventive hair conditioning composition is from about 0.2% to about 2.5%, preferably about 0.3% to about 1.8%, most preferably about 0.5% to about 1.2%, by weight.

The mixture of the foregoing essential hair conditioning agents exhibits high conditioning values and the resultant high value is thought to be due to coaction between the materials. More specifically, when used as the sole conditioning agent in the inventive compositions, the maximum conditioning value noted in the conditioning evaluation hereinafter described is 3 or 4, but in combination a value of 7 is obtained. Such improved conditioning is unexpected.

Thickener

The third essential component in the inventive hair conditioner compositions is the water-soluble nonionic cellulose polymer thickener ingredient. Suitable cellulose polymers include hydroxyethylcellulose, methylcellulose, ethylcellulose and hydroxypropylmethylcellulose, with hydroxyethylcellulose being preferred. The degree of substitution of hydroxyethyl groups on a molar basis is 1.5 to 3. A particularly preferred hydroxyethylcellulose is available under the tradename Natrosol 250 HHR. It has a molar substitution of 2.5 and a 1% solution in water yields a viscosity in water of from 3,400 to 5,000 cps at 24° C. using a Brookfield Viscometer.

The cellulose polymers are employed to control the viscosity of the resultant hair conditioning composition. The proportion of nonionic cellulose polymer in the hair conditioning composition is about 0.8% to about 1.4%, preferably about 1% to about 1.4%, most preferably about 1.1% to 1.3%, by weight.

Solvent

The fourth essential ingredient in the inventive hair conditioning compositions is a dipolar solvent selected from the group consisting of propylene glycol, glycerol, dipropylene glycol, butylene glycol, lanolin acetate and water soluble lanolin derivatives, e.g., ethoxylated lanolin. This ingredient is effective to solubilize the conditioning agents herein in the aqueous medium. A preferred solvent is propylene glycol which is a clear, viscous, colorless liquid which is hygroscopic and completely miscible with water. Also, propylene glycol can penetrate the hair shaft and remain there after rinsing. The amount of solvent employed in the hair conditioner composition is about 0.5% to 2.0%, preferably about 0.8% to about 1.6%, and most preferably about 0.9% to about 1.1%, by weight.

Aqueous Medium

The final essential ingredient in the inventive hair conditioning composition is an aqueous medium which is primarily water, preferably deionized water. Since some of the C8–C22 alkyl tri-C1–C3 alkyl quaternary salts may be supplied in admixtures with a C2–C3 alcohol, e.g., isopropanol, the aqueous medium may contain a small amount of said C2–C3 alcohol. Further, if desired, additional amounts of said C2–C3 alcohol may be added to the composition although generally it is desirable to minimize the amounts of ethanol and isopropanol present. The proportion of the aqueous medium is in the range of about 75.3% to about 98.2%, preferably about 87.9% to about 97%, most preferably about 91.7% to about 96.0%, by weight of the hair conditioning composition.

Preferred Optional Ingredients Optional additional ingredients which desirably are included in the preferred hair conditioning compositions are additional hair conditioning agents selected from the group consisting of (a) mono-C8–C22 alkyl tri-C1–C3 alkyl quaternary ammonium salts, (b) a water-soluble cationic polymer conditioning agent, (c) a C10–C18 alkanol ethoxylate having an HLB in the range of about 6.0 to 12.0 and (d) mixtures of the foregoing. These added hair conditioning agents result in enhanced hair conditioning effects at use concentrations. Typically, preferred compositions will include hair conditioning agents (a) and (b) above, with the most preferred compositions containing agents (a), (b) and (c).

The mono-C8–C22 alkyl tri-C1–C3 alkyl quaternary ammonium salt which preferably is present in the inventive hair conditioning compositions has the following formula:

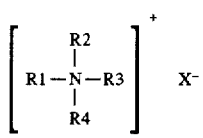

wherein R1 is a higher C8–C18 alkyl group; R2, R3 and R4 are each a C1–C3 alkyl and X is an anion selected from the group consisting of chloride, bromide, methosulfate and ethosulfate. These compounds are water-soluble to varying degrees, with the higher molecular weight homologs generally being less soluble. Also, these ingredients lower the surface tension of water and are good antistatic agents. Preferably, the higher alkyl group will be C14–C18 alkyl, the lower alkyl groups will be methyl and the anion will be chloride. Suitable compounds include trimethylcocoammonium chloride, trimethyhexadecylammonium chloride, trimethyltallowammonium methosulfate and trimethylstearylammonium chloride, with tri-methylhexadecyl ammonium chloride—cetrimonium chloride according to the CTFA Cosmetic Ingredient Dictionary—being most preferred. The proportion of this added quaternary ammonium conditioning agent generally will be about 0.05% to about 1.0%, preferably about 0.05% to about 0.50%, most preferably about 0.06% to about 0.3% by weight of hair conditioning composition.

The optional hair conditioning cationic polymer which preferably is present in the inventive conditioning compositions is selected from the group consisting of natural cellulose cationic polymers and non-cellulosic cationic polymers. Generally, these cationic polymers are water-soluble or, at a minimum, are soluble in the resultant composition. Satisfactory cationic polymers have a molecular weight of from 1,000 to about 1,000,000, preferably 2,000 to 500,000. Usually, the lower the molecular weight, the higher the degree of substitution by the cationic, usually quaternary, group.

Suitable natural polymers which may be converted into the desired cationic polymers are hydroxy alkyl celluloses and alkyl hydroxy alkyl celluloses. Cationic hydroxy alkyl celluloses and their preparation are described in British Pat. No. 1,166,062 of Union Carbide. These cationic hydroxyethylcelluloses are marketed under the trade designation JR 125, JR 30M and JR 400 and are believed to have a molecular weight of 150,000 to 400,000 and a degree of substitution of a quaternary group of about 0.3. Alkyl hydroxy alkyl celluloses having the same formula as hydroxy alkyl cellulose, but with additional alkyl substituents at other sites on the anhydroglucose unit also are available. More particularly, the cationic ethylhydroxyethylcelluloses are available under the tradename "Modocoll" with a molecular weight in the range of 50,000 to 500,000 and a degree of substitution of about 0.1 to 0.8. The preferred cationic cellulose polymer is Polyquaternium 10 which is a polymeric guaternary ammonium salt of hydroxyethylcellulose reacted with a trimethyl ammonium substituted epoxide.

Exemplary of the cationic non-cellulose polymers are the dialkyldiallyl ammonium salt (e.g., halide) homopolymers or copolymers, e.g., dimethyldiallyl ammonium chloride homopolymer, dimethyldiallyl ammonium chloride/acrylamide copolymer and dimethyldiallyl ammonium chloride/acrylic acid copolymer. Preferred polymers include the homopolymer of dimethyldiallyl ammonium chloride sold under the tradename Merquate® 100 (Polyquaternium 6) having a charge density of 126, the copolymer of dimethyldiallyl ammonium chloride and acrylamide sold under the tradename Merquat® 550 (Polyquaternium 7) and the copolymer of dimethyldiallyl ammonium chloride and acrylic acid sold under the tradename Merquat® 280 (Polyquaternium 22), with a mixture of Merquats® 100 and 550 being the most preferred cationic polymer. The proportion of the cationic polymer ingredient generally will be about 0.01% to about 1.5%, preferably about 0.03% to about 0.6%, most preferably about 0.05% to about 0.4%, by weight of the hair conditioning composition.

The optional nonionic hair conditioning agent which preferably is present in the hair conditioning compositions is a C10–C18 alkanol ethoxylate having an HLB in the range of about 6.0 to 12.0. The term "HLB" refers to the hydrophilic/lyophilic balance in the molecule and was developed by Atlas. Suitable nonionic compounds include decyl alcohol ethoxylate (5 EO), lauryl alcohol ethoxylate (6 EO), stearyl alcohol ethoxylate (4 EO) and lauryl alcohol ethoxylate (4 EO). Preferred alkanol ethoxylates contain 12 to 14 carbon atoms in the alkanol group and the most preferred compound is lauryl alcohol ethoxylate (6 EO). The proportion of said alkanol ethoxylate in the hair conditioning composition generally will be about 0.25% to about 5.0%, preferably about 0.5% to about 3.0%, most preferably about 0.75% to about 2.0%, by weight.

A further preferred optional ingredient in the inventive hair conditioning compositions is a polydimethyl siloxane-polyether copolymer having a viscosity in the range of 100 centistokes (cst) to 3000 cst @ 24° C. Such copolymers bear the CTFA designation dimethicone copolyol and satisfactory dimethicone copolyols are sold under the tradename Dow Corning® Q2-5220. This material is present in a non-conditioning proportion which generally is about 0.05% to about 1.5%, preferably about 0.075% to about 1.0%, most preferably about 0.1% to about 0.5%, by weight of the hair conditioning composition. When present, the dimethicone copolyol provides shine to the hair.

In addition to the foregoing preferred optional ingredients, the inventive hair conditioning compositions also may contain additional conventional components such as coloring agents, perfumes, preservatives such as Kathon CG®, sequestering agents and brighteners such as Uvinul. Further, if desired, an opacifying agent such as ethylene glycol mono- or distearate may be included in an opacifying amount. The total weight of these optional additives usually does not exceed 3% by weight of the composition, with the proportion of individual ingredients often being less than 1% by weight.

The hair conditioning compositions of the present invention generally will be in the form of a clear or transparent pourable liquid having a viscosity of about 2,000 to 10,000, preferably 4,000 to 8,000, most preferably about 5,000 to about 7,000, centipoises as measured using a Brookfield Viscometer with a #4 spindle rotating at 20 rpm at 24° C. Usually, the pH will be in the range of 2.5 to about 4.3 at 24° C. and preferably in the range of about 3.5 to about 4.25. Where necessary, the pH will be adjusted using aminomethylpropanol or aminomethylpropanediol.

The inventive conditioners are prepared by admixing the thickener with water at a temperature in the range of about 10° C. to about 60°0 C. using sufficient agitation until a clear, homogeneous mixture is formed. The solvent ingredient is admixed with the C10–C14 alkyl ethoxy methyl carboxylic acid and the mono-C12–C22 alkyl, mono-C1–C3 alkyl ethoxylated quaternary salt ingredient with agitation in another mixing vessel to form a single phase liquid mixture and the latter mixture is added to the homogeneous mixture of thickener and water with agitation at a temperature in the range of about 10° C. to about 60° C. to form a single phase composition. Optionally, the perfume is included in the solvent mixture. Thereafter, preservative and color and opacifier, if any, are added sequentially to said single phase composition with agitation and the pH is adusted as required to form the inventive hair conditioning composition. During the manufacturing process, mixing is controlled to avoid foaming.

In the preferred process, the composition is prepared without the addition of external heat. In the preferred process, the process temperature is controlled in the range of about 20° C. to about 30° C. Use of the so called "cold process" saves energy and the time required to raise or lower the temperature.

The conditioning properties are determined by combing hair tresses treated with the product using the fine teeth of the comb when wet and after drying. In this evaluation, 3.2 gm tresses of virgin, European brown hair obtained from DeMeo Brothers, Inc., are prepared with the root end of the hair at the top of the tress. The tresses are rinsed with running tap water at 40.5° C. and then 1 cc of the test product is worked into the tress with the fingers for one minute. The treated tress is rinsed for 30 seconds and a second application of test product is worked into the tress for one minute followed by a 30 second rinsing. Then each tress is rinsed for 60 seconds with 40.5° C. running tap water and detangled by combing with the wide teeth of the comb. The wetted tresses are maintained wet with deionized water and are combed by expert judges using the fine teeth of the comb. The judges assign a rating of 1 to 10 for each tress, with 10 being easiest to comb and 1 representing no conditioning effect. Each tress is combed by a minimum of 10 judges and the ratings averaged. In the described procedure, the hair tresses are evaluated while wet. The procedure for dry combing is identical except that the hair tresses are dried before being combed.

In the test for evaluation of static, the hair tresses are treated with product as described above and dried. The dried tress is then combed by a skilled evaluator in a forceful, downward manner 20 times using the fine teeth of the comb. The static on each is then evaluated on a scale of 1 to 10 with 10 being excellent. Again, each tress is combed by 10 judges and the ratings are averaged. This evaluation is carried out in a constant temperature-constant humidity room.

Shine properties of the inventive compositions can be evaluated using a visual shine test as well as a light scattering machine. In the visual test, treated tresses are evaluated by trained evaluators using a method which keeps the light intensity constant and the angle between the observor and the object constant. In the light scattering machine, a single hair is held taut and irradiated with light at a prechosen angle and and the amount of reflected light is measured.

While the inventive hair conditioning compositions are single phase at 24° C., the compositions apparently are thermodynamically stable based on the results of aging for up to three months at −18° C., 0° C., 43° C. and 49° C.

The following examples merely illustrate the invention, but it is understood that the invention is not limited thereto. All amounts of the various ingredients in the examples and elsewhere in the specification are percentages by weight unless otherwise specified.

EXAMPLE 1

Example 1 describes a clear hair conditioning composition in accordance with the invention.

|  | % by wt. |
| --- | --- |
| Hydroxyethylcellulose | 1.2 |
| Propylene glycol | 1.0 |
| Ethoquat 18/25 ® (15 EO) (1) | 1.0 |
| Laureth-3 carboxylic acid (3 EO) | 1.0 |
| Water, perfume, color, preservative | q.s. |
|  | 100.00 |

(1) Stearyl polyethoxy dimethyl ammonium chloride

The foregoing composition is prepared by dispersing the hydroxyethylcellulose in water with agitation followed by the addition of a premix of propylene glycol, Ethoquat® 8/25 and laureth-3 methyl carboxylic acid. Said composition is clear at room temperature at pH 3.0 and has a viscosity of 6,000 cps. as measured with a Brookfield Viscometer rotating at 20 rpm using a #4 spindle at 24 C. When this composition is evaluated for conditioning using the above described test, a conditioning value of 7 is obtained.

For comparison purposes, the composition of Example 1 without the ethoxylated quaternary ammonium chloride and the laureth-3 methyl carboxylic acid ethoxylate exhibits a conditioning value of 1 in the described test for hair conditioning.

EXAMPLE 2–10

The improved conditioning properties of the inventive compositions such as Example 1 are apparent from the conditioning results obtained using the prior art hair conditioner compositions set forth in the following examples.

|  | % by wt. | | |
| --- | --- | --- | --- |
|  | Ex. 2 | Ex. 3 | Ex. 4 |
| Hydroxyethyl cellulose | 1.2 | 1.2 | 1.2 |
| Propylene glycol | 1.0 | 1.0 | 1.0 |
| Cetrimonium chloride | 0.5 | — | — |
| Polyquaternium 6 (2) | — | 0.36 | — |
| Polyquaternium 7 (3) | — | — | 0.16 |
| Water, perfume, color, preservative | q.s | q.s. | q.s. |
|  | 100.0 | 100.0 | 100.0 |
| Conditioning value | 3.0 | 3.5 | 3.5 |

(2) Homopolymer of dimethyl diallyl ammonium chloride sold under the tradename Merquat ® 100.
(3) Copolymer of dimethyl diallyl ammonium chloride and acrylamide sold under the tradename Merquat ® 550 as an 8% active material.

The compositions of Examples 2–4 provide about one half of the conditioning properties as the inventive composition of Example 1. Furthermore, when the concentrations of the conditioning compounds in Examples 2–4 are reduced by 50% by weight, the conditioning values are essentially the same, namely 3.0, 3.5 and 2.5 respectively. Such results suggest that higher concentrations of the quaternary ammonium salts and polyquaternary ammonium salts—each well known conditioning agents—would not result in higher hair conditioning properties.

EXAMPLE 5-7

|  | % by wt. | | |
| --- | --- | --- | --- |
|  | Ex. 5 | Ex. 6 | Ex. 7 |
| Hydroxyethyl cellulose | 1.2 | 1.2 | 1.2 |
| Propylene glycol | 1.0 | 1.0 | 1.0 |
| Lauryl alcohol ethoxylate (6 EO) | 2.0 | — | — |
| Dimethicone copolyol (4) | — | 0.2 | 0.4 |
| Water, perfume, color, preservative | q.s. | q.s. | q.s. |
|  | 100.0 | 100.0 | 100.0 |
| Conditioning value | 3.0 | 1.0 | 1.0 |

(4) A polysiloxane substituted with ethoxy and/or propoxy groups sold under the tradename Q-2-5220 ® resin modifier by Dow Corning.

The composition of Example 5 containing 3% by weight of lauryl alcohol ethoxylate (6EO) as the conditioning agent yields a conditioning value of 3.0 which is less than half of value obtained by the inventive compositions. In addition, when the concentration of lauryl alcohol ethoxylate (6EO) is increased to 3% by weight, the conditioning value in the described test still is 3.0, indicating again that increased proportions of said material will not achieve improved conditioning. The compositions of Examples 5 and 6 show that the low concentrations of silicone copolyol have no conditioning properties.

While the improved conditioning properties resulting from use of the inventive compositions is not understood, Examples 8-13 below suggest that the improved conditioning values are the result of coaction of the higher alkyl ethoxylated quaternary ammonium salt and the laureth-3 methyl carboxylic acid ethoxylate.

|  | % by wt. | | |
| --- | --- | --- | --- |
|  | Ex. 8 | Ex. 9 | Ex. 10 |
| Hydroxyethyl cellulose | 1.2 | 1.2 | 1.2 |
| Propylene glycol | 1.0 | 1.0 | 1.0 |
| Ethoquad ® 18/25 (15 EO) (1) | 0.5 | 1.0 | 2.0 |
| Water, perfume, color, preservative | q.s. | q.s. | q.s. |
|  | 100.0 | 100.0 | 100.0 |
| Conditioning value | 2.5 | 3.0 | 3.0 |

Examples 8-10 show that use of Ethoquad®18/25 (15 EO) as the sole conditioning agent results in a conditioning value in the conditioning test described herein at use concentrations of 3.0; and that increasing the concentration from 1% by weight to 2% by weight does not improve the hair conditioning properties.

|  | % by wt. | | |
| --- | --- | --- | --- |
|  | Ex. 11 | Ex. 12 | Ex. 13 |
| Hydroxyethyl cellulose | 1.2 | 1.2 | 1.2 |
| Propylene glycol | 1.0 | 1.0 | 1.0 |
| Laureth-3 methyl carboxylic acid | 0.5 | 1.0 | 2.0 |
| Water, perfume, color, preservative | q.s. | q.s. | q.s. |
|  | 100.0 | 100.0 | 100.0 |
| Conditioning value | 3.0 | 4.0 | 4.0 |

Examples 11-13 show that compositions containing laureth-3 methyl carboxylic acid as the sole conditioning agent are effective to provide a hair conditioning value of 4.0 in the hair conditioning test described herein. Again, increasing the concentration of this material from 1% by weight to 2% by weight does not provide any improvement in conditioning.

When the conditioning properties of the inventive composition set forth in Example 1 are contrasted with the conditioning properties achieved using Ethoquad® 18/25 (15 EO) as the sole conditioning agent—Examples 8-10—or laureth-3 methyl carboxylic acid as the sole conditioning agent—Examples 11-13—, it is apparent that the improved conditioning properties must be due to coaction between said conditioning agents.

EXAMPLE 14

A particularly preferred inventive composition has the formula which follows:

|  | % by Wt. |
| --- | --- |
| Hydroxyethyl cellulose | 1.2 |
| Propylene glycol | 1.0 |
| Ethoquad R 18/25 (15 EO) | 1.0 |
| Lauryl alcohol ethoxylate (6 EO) | 1.0 |
| Cetrimonium chloride | 0.0625 |
| Polyquaternium 6 (2) | 0.12 |
| Polyquaternium 7 (3) | 0.04 |
| Laureth-3 methyl carboxylic acid | 1.0 |
| Dimethicone copolyol | 0.2 |
| Water, perfume, color, preservative | q.s. |
|  | 100.0 |
| Conditioning value | 10.0 |

The foregoing composition illustrates that the addition of a water-soluble quaternary ammonium salt, e.g., cetrimonium chloride, a nonionic compound, e.g., lauryl alcohol ethoxylate (6EO), two cationic conditioning polymers, e.g., Polyquaternium 6 and 7, and a water-soluble silicone to the inventive compositions results in a hair conditioning composition which provides optimum conditioning as evidenced by a value of 10—the highest value—in the described hair conditioning test. When the composition of Example 14 is repeated with the omission of the lauryl alcohol ethoxylate and the laureth-3 methyl carboxylic acid and an increase in Polyquaternium 7 to 0.08% by weight, the resultant composition exhibits a conditioning value of 5.5. Such result again shows the need for the mixture of the higher alkyl ethoxylated quaternary ammonium salt and the laureth-3 methyl carboxylic acid as the conditioning agent.

EXAMPLE 15

When the composition of Example 14 is prepared with the omission of Polyquaterniums 6 and 7 and the dimethicone copolyol—said ingredients being replaced by water—, the resultant hair conditioner exhibits a conditioning value of 8.5 in the described hair conditioning test.

Other particularly preferred hair conditioning compositions in accordance with the described invention are set forth in Examples 16-18 which follow.

EXAMPLE 16-18

|  | % by wt. | | |
| --- | --- | --- | --- |
|  | Ex. 16 | Ex. 17 | Ex. 18 |
| Hydroxyethyl cellulose | 1.2 | 1.2 | 1.2 |
| Propylene glycol | 1.0 | 1.0 | 1.0 |
| Ethoquad R 18/25 (15 EO) | 1.0 | 1.0 | 1.0 |
| Lauryl alcohol ethoxylate (6 EO) | 1.0 | 1.0 | 1.0 |
| Dimethicone copolyol | 0.2 | 0.2 | 0.2 |

11

-continued

| | % by wt. | | |
|---|---|---|---|
| | Ex. 16 | Ex. 17 | Ex. 18 |
| Cetrimonium chloride | 0.0625 | 0.0625 | 0.0625 |
| Polyquaternium 6 (2) | 0.12 | 0.08 | 0.04 |
| Polyquaternium 7 (3) | 0.04 | 0.04 | 0.04 |
| Laureth-3 carboxylic acid (3 EO) | 1.0 | 0.75 | 0.5 |
| Aminomethyl propanol | 0.1 | 0.1 | 0.1 |
| Water, perfume, color, preservative | q.s. | q.s. | q.s. |
| | 100.0 | 100.0 | 100.0 |
| Conditioning value | 10.0 | 10.0 | 10.0 |

The addition of the aminomethyl propanol increases the pH of the inventive compositions from 2.5–3.0 to between 3.5 and 4.25 and improves the viscosity stability at elevated temperatures, e.g., 49° C. The viscosity at 24° C. is between 5,000 cps. and 7,000 cps. as measured by a Brookfield Viscometer using a #4 spindle rotating at 20 rpm.

As stated heretofore, the inventive hair conditioning compositions are clear—single phase—at room temperature (24° C.) and are thermodynamically stable. Clarity is achieved because said compositions are free of water-insoluble C12–C22 alkanol conditioning agents and of conditioning amounts of silicone conditioning agents which are not soluble in the compositions. Typically, most silicone hair conditioning agents are water-insoluble and are not soluble in the hair conditioning composition.

Also within the scope of the present invention is a method of conditioning hair comprising the steps of contacting the hair with an effective amount of a single phase composition comprising a mixture of a nonionic cellulose polymer thickener, a dipolar solvent, a mono-C12–C22 alkyl monomethyl ethoxy substituted quaternary ammonium salt conditioning agent containing 10 to 20 ethenoxy groups in the molecule and a C10–C18 alkyl ethoxy methyl carboxylic acid having 1 to 23 ethoxy groups in the molecule in an aqueous medium, distributing said composition throughout the hair and combing said hair. The hair may be either wet or dry when said conditioning composition is applied thereto. An effective amount may be from 1–10 grams, preferably 2 to 6 grams of the inventive hair conditioner composition which either may be applied directly to the hair or, alternatively, may be mixed with water prior to application to the hair.

What is claimed is:

1. A single phase hair conditioning composition having improved hair conditioning properties comprising, by weight, about 0.8% to 1.4% of a water-soluble nonionic cellulose polymer as a thickener; about 0.5% to about 2.0% of a dipolar solvent selected from the group consisting of propylene glycol, butylene glycol, glycerol, dipropylene glycol, lanolin acetate and water soluble lanolin derivatives; about (0.2% to about 3.0% of a water soluble mono-C12–C22 alkyl, monomethyl ethoxy substituted quaternary ammonium salt conditioning agent containing from 10 to 20 ethoxy groups in the molecule; about 0.2% to about 2.5% of a C10–C10–C18 alkyl ethoxy methyl carboxylic acid having 1 to 23 ethoxy groups in the molecule; and the balance being an aqueous medium; said composition being free of water-insoluble C12–C22 alkanol conditioning agents and of conditioning amounts of silicone conditioning agents.

2. A hair conditioning composition according to claim 1 which includes in addition a hair conditioning agent selected from the group consisting of:
(a) about 0.05% to about 1.0% of a water-soluble mono-C8–C22 alkyl tri-C1–C3 alkyl quaternary ammonium salt;

12

(b) about 0.01% to about 1.5% of a water-soluble cationic polymer conditioning agent;
(c) about 0.25% to about 5.0% of a C10–C18 alkanol ethoxylate nonionic conditioning agent having an HLB in the range of about 6.0 to about 12; and
(d) mixtures of the foregoing.

3. A hair conditioning composition according to claim 2 wherein said added conditioning agent is a mixture of (a) and (b).

4. A hair conditioning composition according to claim 2 wherein said added conditioning agent is a mixture of (a), (b) and (c).

5. A hair conditioning composition according to claim 2 which includes in addition a non-conditioning amount of about 0.05% to about 1.5% of a dimethicone copolyol as a shine agent.

6. A hair conditioning composition according to claim 1 wherein said water-soluble nonionic cellulosic thicker is selected from the group consisting of hydroxyethylcellulose, methylcellulose, ethylcellulose and hydroxypropylmethylcellulose.

7. A hair conditioning composition according to claim 1 wherein said dipolar solvent is selected from the group consisting of propylene glycol, glycerol, dipropylene glycol, butylene glycol, lanolin acetate and water-soluble lanolin derivatives.

8. A hair conditioning composition according to claim 1 wherein said water soluble mono-C12–C22 alkyl, monomethyl ethoxy substituted quaternary ammonium salt conditioning agent containing from 10 to 20 ethoxy groups in the molecule has 16 to 22 carbon atoms in the alkyl group.

9. A hair conditioning composition according to claim 1 wherein said methyl carboxylic acid has 2 to 10 ethoxy groups in the molecule.

10. A hair conditioning composition according to claim 1 wherein said nonionic polymer is present in an amount of about 1% to about 1.4% by weight, said solvent is present in an amount of about 0.8% to about 1.6% by weight, said ethoxylated quaternary ammonium salt is present in an amount of about 0.3% to about 2.2% by weight, said alkyl ethoxy methyl carboxylic acid is present in an amount of about 0.3% to about 1.8% by weight and said aqueous medium is present in an amount of about 87.9% to about 97.6% by weight.

11. A hair conditioning composition according to claim 6 which includes, in addition, a hair conditioning agent selected from the group consisting of:
(a) about 0.05% to about 1.0% by weight of a water-soluble mono-C8–C22 alkyl, tri-C1–C3 alkyl quaternary ammonium salt;
(b) about 0.01% to about 1.5% by weight of a water-soluble cationic polymer conditioning agent;
(c) about 0.25% to about 5.0% by weight of a C10–C18 alkanol ethoxylate nonionic conditioning agent having an HLB in the range of 6.0 to 12.0; and
(d) mixtures of the foregoing.

12. A hair conditioning composition according to claim 11 wherein said added conditioning agent is a mixture of (a) and (b).

13. A hair conditioning composition according to claim 11 wherein said added conditioning agent is a mixture of (a), (b) and (c).

14. A hair conditioning composition according to claim 11 which includes in addition a non-conditioning amount of about 0.05% to about 1.5% of a dimethicone copolyol as a shine agent.

15. A single phase hair conditioning composition having improved hair conditioning properties comprising, by weight, about 1% to about 1.4% of hydroxyethyl cellulose thickener; abut 0.8% to about 1.6% of propylene glycol solvent; about 0.3% to about 2.2% of mono-C14–C18 alkyl methyl ethoxylated quaternary ammonium salt containing 10 to 20 ethenoxy groups in the molecule; about 0.3% to about 1.8% of C10–C14 alkyl ethenoxy methyl carboxylic acid having 2 to 10 ethoxy groups in the molecule; about 0.05% to about 0.5%, of C14–C18 alkyl trimethyl quaternary ammonium salt; about 0.03% to about 0.6%, of a cationic polymer conditioning agent selected from the group consisting of Polyquaternium 6, Polyquaternium 7, Polyquaternium 10, Polyquaternium 22 and mixtures thereof; about 0.5% to about 3.0% of a C10–C14 alkanol ethoxylate nonionic conditioning agent having an HLB in the range of 6 to 12; and about 87.9% to about 97.0% of an aqueous medium comprising water, said composition being free of water-insoluble C12–C22 alkanol conditioning agents and of conditioning amounts of silicone conditioning agents.

16. A hair conditioning composition according to claim 15 which includes in addition a non-conditioning amount of about 0.075% to about 1.0% by weight of dimethicone copolyol as a shine agent.

17. A hair conditioning composition according to claim 15 wherein said hydroxyethylcellulose is present in an amount of about 1.1% to about 1.3%; said propylene glycol is present in an about of about 0.9% to about 1.1% said ethoxylated carboxylic acid is present in an amount of about 0.5% to about 1.2%; said cationic polymer is a mixture of Polyquaternium 6 and Polyquaternium 7 present in an amount of about 0.05% to about 0.4%; said nonionic conditioning agent is a lauryl alcohol ethoxylate present in an amount of about 0.75% to about 2.0%; said aqueous medium is present in an amount of about 91.7% to abut 96.0%; and said composition includes in addition about 0.1% to about 0.5% by weight of dimethicone copolyol.

18. A method of conditioning the hair which comprises the steps of contacting hair with the composition of claim 1, distributing said composition throughout the hair and combing the treated hair.

* * * * *